United States Patent [19]

Whitlock

[11] 4,319,573

[45] Mar. 16, 1982

[54] PERSONAL LIQUID REMOVAL SYSTEM

[76] Inventor: Norris W. Whitlock, 105 Creekside Ct., Greer, S.C. 29651

[21] Appl. No.: 123,666

[22] Filed: Feb. 22, 1980

[51] Int. Cl.³ .............................................. A61M 1/00
[52] U.S. Cl. .................................. 128/295; 128/272; 128/275
[58] Field of Search ............... 128/DIG. 24, 272, 276, 128/277, 278, 295, 296, 214 D, 214 E, 214 F, 760, 762, 764, 766, 767, 275; 4/144.1, 144.2, 144.3, 144.4

[56] References Cited

U.S. PATENT DOCUMENTS

| | | | |
|---|---|---|---|
| 1,229,423 | 6/1917 | Eckenrode | 128/295 |
| 2,476,375 | 7/1949 | Kent | 128/295 |
| 2,640,484 | 6/1953 | Johnson | 128/295 |
| 3,415,299 | 12/1968 | Hinman, Jr. et al. | 128/275 |
| 3,881,486 | 5/1975 | Fenton | 128/295 |

FOREIGN PATENT DOCUMENTS

| | | | |
|---|---|---|---|
| 471130 | 8/1974 | Australia | 128/295 |
| 529812 | 11/1940 | United Kingdom | 128/295 |

Primary Examiner—Robert W. Michell
Assistant Examiner—J. L. Kruter
Attorney, Agent, or Firm—Larry Harold Kline

[57] ABSTRACT

A device is disclosed for storing liquid material being removed from a person by a tube which comprises a first container secured to the person and operative to hold the liquid material, a first valve means secured in the bottom of the first container, and first connecting means secured to the first valve means.

29 Claims, 10 Drawing Figures

PERSONAL LIQUID REMOVAL SYSTEM

This invention relates to bags for contaminated wastes and more particularly to a bag system which can be utilized with a leg bag and an overnight bag.

There are many patients who, due to injury or disease, are confined to wheel chairs or are in a condition where it is necessary to utilize bags which are connected to a urinary catheter for collection of waste materials. Presently a leg bag may be attached to the person with the leg bag being removed at night and a larger overnight bag being attached in its place.

The present invention allows the leg bag to remain in place and provides a connection from the leg bag to an overnight bag thereby avoiding the detachment of the catheter from the leg bag which might open the system of the person to infection.

An object of the present invention is to reduce the amount of contamination of bacteria to the urinary bladder that may arise because of the repeated disconnection of the catheter drainage system.

Another object of this invention is to modify valves used in contaminated waste bags so that the bag is easier to use for disabled patients.

Still another object of this invention is to improve valves used with urinary waste bags so that there is less likelihood for contamination.

Another object of this invention is to provide a sampling port above the level of the contaminated wastes so that urinary samples can be taken without risk of infection or contamination.

Another object of this invention is to provide injection ports in contaminated waste bags for the injection of chemicals to improve the aesthetic quality of life or the bacteriological count within the bags and to improve their longevity and usefulness.

Still another object of this invention is to provide a sloped lower portion of a contaminated waste bag in order to increase proper drainage and to decrease the possibility of having residue or sludge accumulate in the bottom of the bag.

A further object of this invention is to provide valves that produce a funnel-type effect and allow better drainage of the contaminated wastes.

These and other objects and features of the invention will be apparent from the following description and appended claims.

Briefly, the invention is a device for storing liquid material which is being removed from a person by a tube. The device comprises a first container which is secured to the person and is operative to hold the liquid material. A first valve means is secured in the bottom of the first container. A first connecting means is secured to the first valve means. A second container may be operative to be connected to the first container and to store the liquid material when the first valve means is open. The first valve means may comprise a first upper closure piece. The first valve means has a first front funnel surface which is basically flat when the first valve means is closed and forms a sloping side when the first valve means is open. A first rear funnel surface is basically flat when the first valve means is closed and forms a sloping side when the first valve means is open. A first right sloping funnel edge connects the right side of the first front funnel surface to the first rear funnel surface. A first left sloping funnel edge connects the left side of the first front funnel surface to the first rear funnel surface. The first valve means further comprises a retainer clip secured to the first upper closure piece and operative to hold the first upper closure piece open when desired by the person. The first upper closure piece comprises a first metal valve, chemically coated, with spring tension on the first metal valve holding the first metal valve closed at rest. The first valve means further comprises a first securing area within the first valve means. A first connector tubing is secured within the first securing area and extends out from the bottom of the first valve means. The first container comprises an inlet port operative to be secured to the tube.

A flutter valve is secured at the input of the first container below the inlet port and is operative to prevent contamination from traveling from the first container back to the inlet port and into the tube. A sampling port is secured within the inlet port wherein liquid material entering the inlet port can be removed without contamination of the tube.

A first injection plug is secured onto the front section of the first container and is operative for solutions to be injected therethrough. The first container further comprises a first disk secured to the rear surface of the first container located opposite from the first injection plug. A syringe needle may penetrate the first injection plug and hit the first disk. The syringe needle will not puncture the rear surface of the first container which would have caused contamination.

A micropore vent is secured onto the front section of the first container and is operative to allow air into the first container while filtering out bacteria. The first container has a first lower right sloping side, a first lower left sloping side, a first lower right rounded corner, and a first lower left rounded corner, all operative to aid in the flow of the liquid material into the first valve means. A first connector tubing is secured within the first valve means and extends out from the bottom of the first valve means. The device further comprises a securing ring attached around the first connecting means and a flexible cap arm secured to the securing ring. A cap is secured to the cap arm. The cap can cover the open portion of the first connecting means when desired by the person to prevent contamination of the first connector tubing. The device further comprises a second connector tubing and a second connecting means secured around the second connector tubing. A first locking mechanism portion is secured to the first connecting means. A second locking mechanism portion is secured to the first connecting means. The first locking mechanism portion may be secured to the second locking mechanism portion thereby securing the first connecting means to the second connecting means and the first connector tubing to the second connector tubing without contaminating the first connector tubing and the second connector tubing. The second upper closure piece comprises a second metal valve, chemically coated, with spring tension on the second metal valve holding the second metal valve closed at rest. The second container further comprises a second injection plug secured onto the front section of the second container and operative for solutions to be injected therethrough. The second container further comprises a second disk secured to the rear surface of the second container located opposite from the second injection plug whereby a syringe needle penetrating the second injection plug would hit the second disk and not puncture the rear surface of the second container. A second valve means is connected at the bottom of the second container and is operative for the liquid material to be removed from the second container when the second valve means is open. The second valve means comprises a second upper closure piece, a second front funnel surface and a second rear funnel surface. The second valve means also comprises a second right sloping funnel edge and a second left sloping funnel edge. The second valve means further comprises a second securing area within the second valve means. Drainage tubing is secured within the second securing area and extends out from the bottom of the second valve means. A first drainage connector is secured to the end of the drainage tubing. A second drainage connector is secured onto the surface of the second container and is operative for the first drainage connector to be secured to when the second valve means is closed and the first drainage connector is not needed, in order to reduce contamination. The second connecting means rest connection is secured onto the surface of the second container. It is operative for the second connecting means to be secured to when the second container is not connected to the first container. The tube may be a catheter. The present invention can be utilized for not only urinary wastes from the body but for any other liquid material in which storage is necessary or desirable.

The invention will be more fully understood from the following detailed description and appended claims when taken with the drawings in which:

FIG. 1 is a partial side elevational view of the leg 2 of a person with the leg contaminated waste bag 1 connected to the leg 2 and to the inflow tubing 32 of the overnight drainage bag 40.

Figure 5:
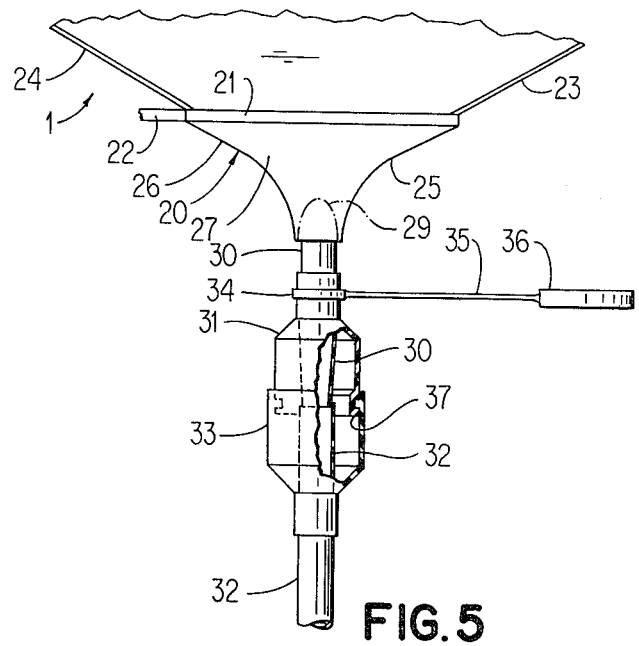

FIG. 5 is an enlarged partial elevational view of the lower portion of the bag 1 and its connection to the inflow tubing 32 of the overnight drainage bag 40 showing a cutaway portion of locking mechanism 37.

Figure 6:
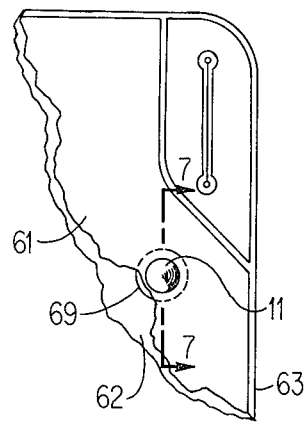

FIG. 6 is a partial elevational view of the upper right side of Bag 1.

Figure 7:
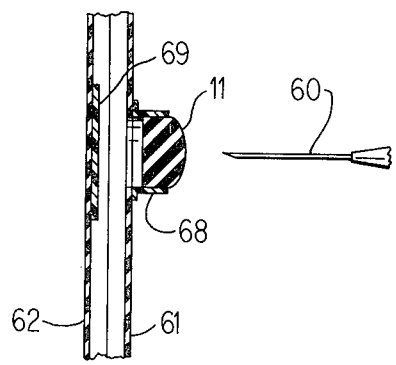

FIG. 7 is a partial side sectional view at section 7—7 of FIG. 6.

Figure 8:
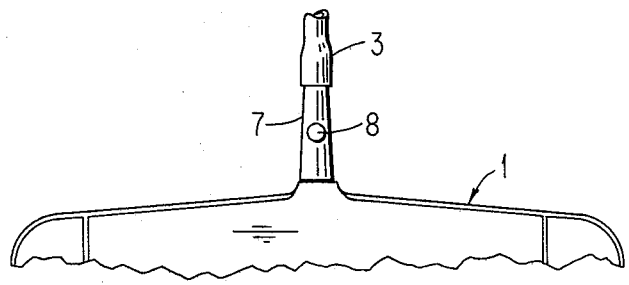

FIG. 8 is a partial elevational view of the top portion of bag 1 and the connections thereto.

Figure 9:
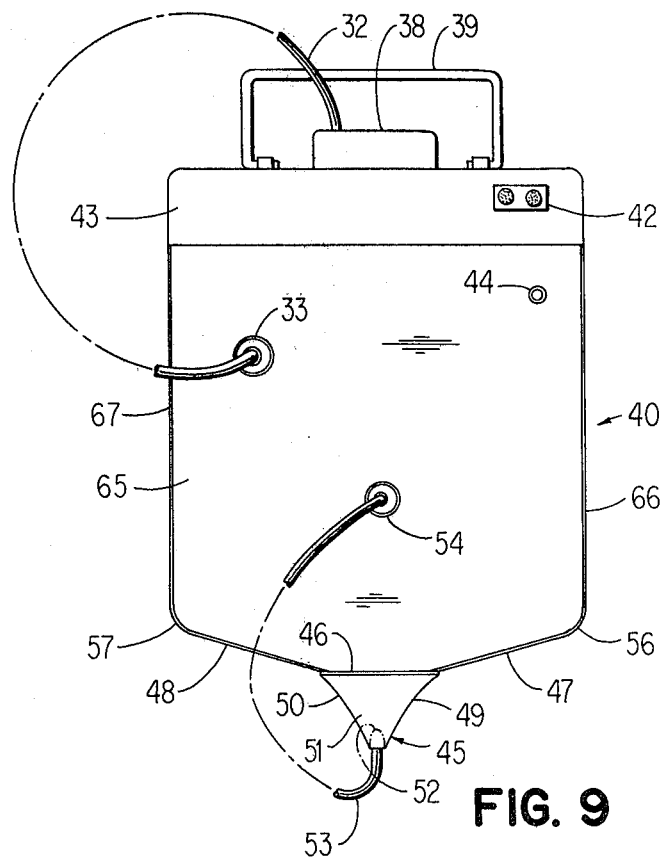

FIG. 9 is a front elevational view of bag 40 with inflow tubing 32 and drainage tube 53 secured onto the front surface 55 of bag 40.

Figure 10:
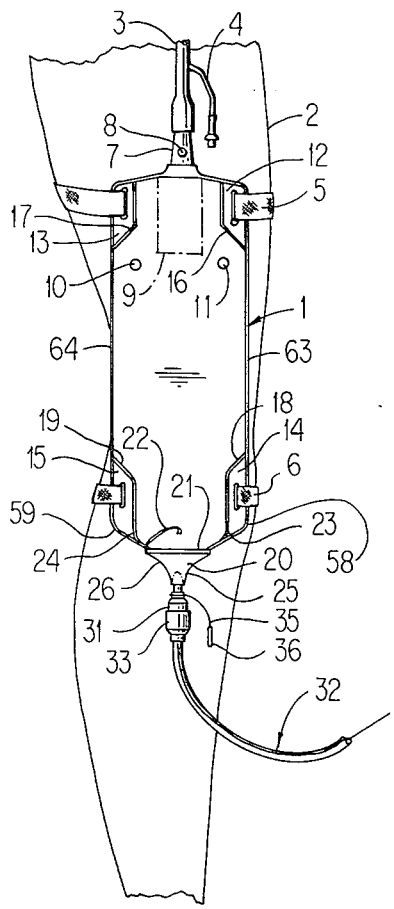
Figure 10:
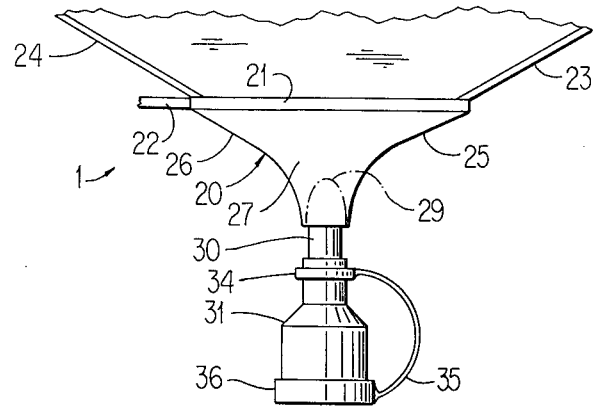

FIG. 10 is an enlarged partial elevational view of the lower portion of bag 1 with bag 1 not connected to bag 40, but with cap 36 secured onto male connector 31.

Figure 1:
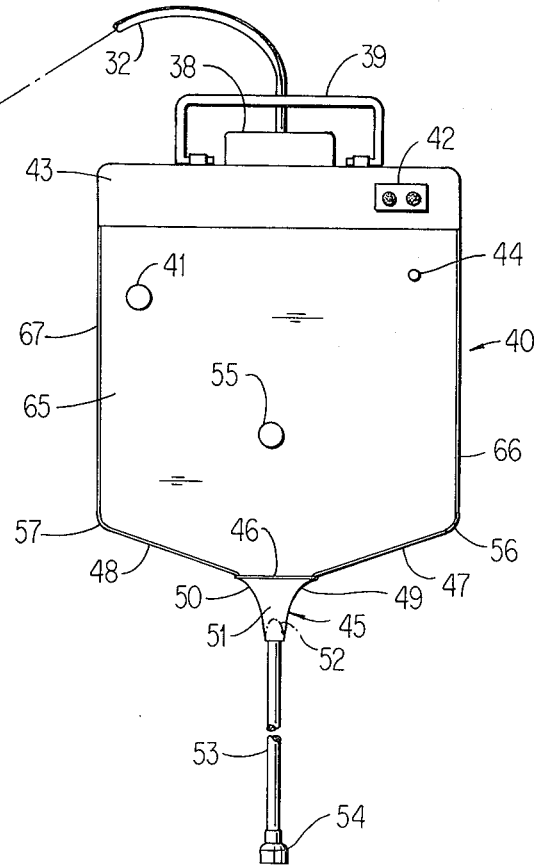

Referring now to the drawings, FIG. 1 shows a partial side elevational view of the leg 2 of a person with the leg contaminated waste bag 1 connected to the leg 2 and to the inflow tubing 32 of the overnight drainage bag 40. The distal portion 3 of the catheter which extends into the person has a balloon arm 4, which is standard in a Foley catheter. Bag 1 is connected to the leg 2 by upper leg strap 5 and lower leg strap 6. Bag 1 has a tapered inlet port 7. In the tapered inlet port 7 is a latex sampling port 8. The latex sampling port 8 is above the flutter valve 9. Samples can be taken from the latex sampling port 8 without damage or contamination from bag 1. The flutter valve 9 is a standard valve which prevents contamination through the tapered inlet port 7. On bag 1 is a vent 10 and an injection plug 11. Vent 10 may be a micropore vent which is basically a filter with small enough pores to allow air in but to filter bacteria out. A micropore filter will break the possibility of a vacuum forming in the bag 1. The upper leg strap 5 extends through the upper right strap slit section 12 and the upper left strap slit section 13. The lower leg strap 6 extends through the lower right strap slit section 14 and the lower left strap slit section 15. Sealing the upper strap slit section 12 from the rest of bag 1 is the upper right seal 16. Sealing the upper left strap slit section 13 from the rest of the bag 1 is upper left seal 17. Sealing the lower right strap slit section 14 from the rest of bag 1 is lower right seal 18. Sealing the lower strap slit section 15 from the rest of bag 1 is lower left seal 19. Drainage valve 20 allows the contaminated wastes within bag 1 to drain from bag 1 when drainage valve 20 is properly opened. Drainage valve 20 has an upper closure piece 21. The upper closure piece 21 may be a silicone rubber coated spring action metal band, holding drainage valve 20 closed at rest. Drainage valve 20 shall be chemically coated.

FIG. 1 shows the bag 1 connected to leg 2 and also shows the connection of the inflow tubing 32 to the overnight drainage bag 40. Bag 40 has a handle 39. Drip chamber 38 on bag 40 prevents refluxing of infected urine. On bag 40 is male connector 41 which is utilized to prevent gross contamination of inflow tubing 32 when the inflow tubing 32 is not connected into bag 1. Male connector 41 is a connecting means rest connection. Bag 40 has a micropore vent assembly 42 on the rigid plastic top assembly 43. Bag 40 has a latex injection plug 44.

Drainage valve 45 is utilized to removed contaminated wastes from bag 40 through drainage tube 53.

Figure 2:
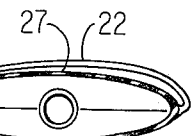
FIG. 2 is a top sectional view of the drainage valve 20 held in the open position by retainer clip 22.

FIG. 2 is a top sectional view of drainage valve 20 held in the open position by a retainer clip 22. The upper closure piece 21 is held in the open position and the front movable funnel surface 27 and rear movable funnel surface 28 form a funnel through which the contaminated wastes flow.

Figure 3:
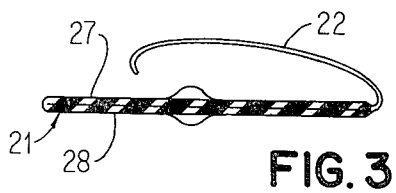
FIG. 3 is a top sectional view of the drainage valve 20 in the closed position.

FIG. 3 shows a top sectional view of the drainage valve 20 in the closed position. Retainer clip 22 has been released and upper closure piece 21 automatically, through spring action, closes. The spring action may be in the tension of the metal itself or in end springs. Other springs devised could be utilized, if desired.

Figure 4:
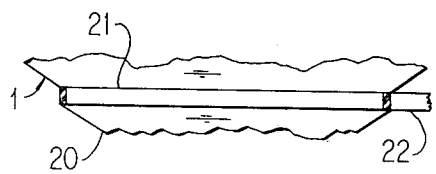
FIG. 4 is a side sectional view of the upper closure piece 21 of drainage valve 20.

FIG. 4 is a side sectional view of the upper closure piece 21 of the drainage valve 20.

FIG. 5 is an enlarged partial elevational view of the lower portion of bag 1 and its connection to the inflow tubing 32 of the overnight drainage bag 40 showing a cutaway portion of the locking mechanism 37.

Bag 1 has a lower right sloping side 23 and a lower left sloping side 24. Sloping sides 23 and 24 aid in the flow of the contaminated wastes towards drainage valve 20. Drainage valve 20 has a right sloping funnel edge 25 and a left sloping funnel edge 26. Funnel edges 25 and 26 aid in the flow of the contaminated wastes through the drainage valve 20. Front movable funnel surface 27 and rear movable funnel surface 28 are basically flat when drainage valve 20 is closed and are sloping when drainage valve 20 is open.

Rigid connector tubing 30 is secured within securing area 29 within drainage valve 20. Male connector 31 is rigidly secured to rigid connector 30. Female connector 33 is rigidly secured to the inflow tubing 32 of the overnight drainage bag 40. The rigid connector 30 is tapered to fit within the inflow tubing 32 when the male connector 31 is secured within the female connector 33. The male connector 31 may be secured within female connector 33 by a bayonet-type locking mechanism 37. Other type locking mechanisms may be utilized.

When connected, rigid connector 30 goes into inflow tubing 32; male connector 31 goes into female connector 33, and both are secured by locking mechanism 37.

A securing ring 34 is attached to male connector 31. Attached to securing ring 34 is cap arm 35. Attached to cap arm 35 is a cap 36 which can fit over male connector 31 to avoid any contamination when male connector is not connected to a female connector such as inflow tubing 32.

FIG. 6 is a partial elevational view of the upper right side of bag 1 showing the latex injection plug 11.

FIG. 7 is a partial side sectional view at section 7—7 of FIG. 6;

The injection plug 11 may be a latex injection plug. A syringe needle 60 may press through the injection plug 11 and inject desired solutions into the bag 1. A similar injection plug 44 is on bag 40. When the needle enters the bag 1, it is prevented by hard plastic disk 69 from perforating the rear surface 62 of bag 1. The needle 60 passes through the front surface 61 of bag 1. The latex injection plug 11 is held on front surface 61 by a hard plastic plug holder 68.

When the needle 60 penetrates the plug 11, solutions can be injected or removed through the syringe. When the needle is removed, the latex closes and maintains a closed system. Sampling may be necessary for monitoring for infection or for injecting solutions to control contamination or smell.

FIG. 8 is a partial elevational view of the top portion of bag 1 and the connections thereto.

Inlet port 7 is tapered to fit within the distal portion of the catheter. If desired, the inlet port 7 of bag 1 can be secured in some manner, either permanent or removable, to the distal portion 3.

If desired, distal portion 3 and inlet port 7 can be tapered or secured in any other manner. The distal portion 3 of the catheter will be of some latex or softer material than the inlet port 7. The distal port 3 will secure over the inlet port 7 as shown on FIG. 8.

In the inlet port 7 is a sampling port 8. The sampling port 8 can be punctured with a needle for withdrawing solution for evaluating purposes. Sampling port 8 is above the flutter valve 9. Theoretically, the solution below the flutter valve 9 is non-sterile and the solution above the flutter valve 9 is sterile. The sampling port 8 allows the solution to be removed while still maintaining a closed system and thereby preventing the possibility of contamination.

FIG. 9 is a front elevational view of bag 40 with the inflow tubing 32 and drainage tube 53 secured onto the front surface 65 of bag 40. When bag 40 is not connected to a bag such as bag 1, the inflow tubing 32 may be secured onto male connector 41 which is located on the front surface 65 of bag 40. The connection in this manner prevents contamination of the inflow tubing 32.

The drainage tube 53 can be secured onto the male connector 55 which is secured onto the front surface 65 of bag 40. Drainage tube 53 has a female connector 54 which connects onto the male connector 55 of bag 40.

Drainage valve 45 is similar to the drainage valve 20 of bag 1. Drainage valve 45 has an upper closure piece 46 which is similar to upper closure piece 21 of bag 1.

Bag 40 has a lower right sloping side 47 and a lower left sloping side 48. Drainage valve 45 has a right sloping funnel edge 49 and a left sloping funnel edge 50. Drainage valve 45 has a front movable funnel surface 51 and a rear movable funnel surface (not shown).

Drainage tube 53 is secured to drainage valve 45 within securing area 52.

Bag 40 has a lower right rounded corner 56 and a lower left rounded corner 57.

Bag 1 has a lower right rounded corner 58 and a lower left rounded corner 59. The rounded corners and the sloping sides help the contaminated wastes to flow better and helps prevent contaminated residue at the bottom of the bags.

Bag 40 has a front surface 65 and a rear surface (not shown). Bag 40 has a right edge 66 and a left edge 67. Bag 1 has a front surface 61 and a rear surface 62. Bag 1 has a right edge 63 and a left edge 64.

FIG. 10 is an enlarged partial elevational view of the lower portion of bag 1. Bag 1 is not connected to bag 40.

Cap 36 is secured onto male connector 31. The placing of cap 36 onto the male connector prevents contamination of the male connector 31 when not in use to connect bag 1 to another bag.

While the invention has been described with reference to specific embodiments, the description is illustrative and is not to be construed as limiting the scope of the invention. Various modifications and changes may occur to those skilled in the art without departing from the spirit and scope of the invention as defined by the appended claims.

I claim:

1. A device, adapted to be secured to a person, for storing liquid material being removed from said person by a tube comprising:
   (a) a first storage container which is secured to said person and is operative to hold said liquid material;
   (b) a first valve means secured in the lower longitudinal portion of said first storage container, said first valve means comprising:
      (1) a first upper closure piece secured in the upper longitudinal portion of said first valve means;
      (2) a first front funnel surface, extending from said upper longitudinal portion of said first valve means to the lower longitudinal portion of said first valve means, and secured to said first upper closure piece, which is basically flat when said first valve means is closed and forms a sloping side when said first valve means is open;
      (3) a first rear funnel surface, extending from said upper longitudinal portion of said first valve means to said lower longitudinal portion of said first valve means, and secured to said first upper closure piece, which is basically flat when said first valve means is closed and forms a sloping side when said first valve means is open;
      (4) a first right sloping funnel edge, secured onto the right transverse portion of said first valve means extending from said upper longitudinal portion of said first valve means to said lower longitudinal portion of said first valve means, and secured to said first upper closure piece, connecting the right side of said first funnel surface to said rear funnel surface;
      (5) a first left sloping funnel edge, secured onto the left transverse portion of said first valve means extending from said upper longitudinal portion of said first valve means to said lower longitudinal portion of said first valve means, and secured to said first upper closure piece, connecting the left side of said first front funnel surface to said first rear funnel surface;

(c) a first connecting means secured to said first valve means; and (d) a first connector tubing secured within said first valve means and extending out from said lower longitudinal portion of said first valve means wherein said first connecting means is secured around said first connector tubing.

2. A device according to claim 1 further comprising a second storage container operative to be connected to said first storage container and to store said liquid material when said first valve means is open.

3. A device according to claim 2 wherein said first valve means comprises a first connector tubing secured within said first valve means and extending out from said lower longitudinal portion of said first valve means wherein first connecting means is secured around said first connector tubing.

4. A device according to claim 3 wherein said device further comprises:
   (a) a second connector tubing;
   (b) a second connecting means secured around said second connector tubing;
   (c) a first locking mechanism portion secured to said first connecting means; and
   (d) a second locking mechanism portion secured to said second connecting means whereby said first locking mechanism portion may be secured to said second locking mechanism portion thereby securing said first connecting means to said second connecting means and said first connector tubing to said second connector tubing without contaminating grossly the first connector tubing and the second connector tubing.

5. A device according to claim 4 wherein said device further comprises a second connecting means rest connection secured onto the surface of said second container and operative for said second connecting means to be secured to when said second container is not connected to said first container, in order to reduce contamination of said second connecting means and said second connector tubing.

6. A device according to claim 4 wherein said first valve means comprises:
   (a) a first upper closure piece secured in the upper longitudinal portion of said first valve means;
   (b) a first front funnel surface, extending from said upper longitudinal portion of said first valve means to the lower longitudinal portion of said first valve means, and secured to said first upper closure piece, which is basically flat when said first valve means is closed and forms a sloping side when said first valve means is open; and
   (c) a first rear funnel surface, extending from said upper longitudinal portion of said first valve means to said lower longitudinal portion of said first valve means, and secured to said first upper closure piece, which is basically, flat when said first valve means is closed and forms a sloping side when said first valve means is open.

7. A device according to claim 2 wherein said device further comprises a second valve means connected at the the lower longitudinal portion of said second container operative for said liquid material to be removed from said second container when said second valve means is open.

8. A device according to claim 7 wherein said second valve means comprises:
   (a) a second upper closure piece secured in the upper longitudinal portion of said second valve means;
   (b) a second front funnel surface, extending from said upper longitudinal portion of said second valve means to the lower longitudinal portion of said second valve means, and secured to said second upper closure piece, which is basically flat when said second valve means is closed and forms a sloping side when said second valve means is open;
   (c) a second rear funnel surface, extending from said upper longitudinal portion of said second valve means to said lower longitudinal portion of said second valve means, and secured to said second upper closure piece, which is basically flat when said second valve means is closed and forms a sloping side when said second valve means is open.

9. A device according to claim 8 wherein said second valve means further comprises:
   (a) a second right sloping funnel edge, secured onto the right transverse portion of said second valve means extending from said upper longitudinal portion of said second valve means to said lower longitudinal portion of said second valve means, and secured to said second upper closure piece, connecting the right side of the said second front funnel surface to said rear funnel surface; and
   (b) a second left sloping funnel edge, secured onto the left transverse portion of said second valve means extending from said upper longitudinal portion of said second valve means to said lower longitudinal portion of said second valve means, and secured to said second upper closure piece, connecting the left side of said second front funnel surface to said second rear funnel surface.

10. A device according to claim 2 wherein said second container further comprises a second lower right sloping side, a second lower left sloping side, a second lower right rounded corner and a second lower left rounded corner, all operative to aid in the flow of said liquid material into said second valve means.

11. A device according to claim 1 wherein said first valve means further comprises a retainer clip secured to said first upper closure piece and operative to hold said first upper closure piece open when desirable to said person.

12. A device according to claim 1 wherein said device further comprises a securing ring attached around said first connecting means, a flexible cap arm secured to said securing ring, and a cap secured to said cap arm wherein said cap can cover the open portion of said first connecting means, when desired by said person, to prevent contamination of said first connector tubing.

13. A device according to claim 1 wherein said device further comprises:
   (a) a second connector tubing;
   (b) a second connecting means secured around said second connector tubing;
   (c) a first locking mechanism portion secured to said first connecting means; and
   (d) a second locking mechanism portion secured to said second connecting means whereby said first locking mechanism portion may be secured to said second locking mechanism portion thereby securing said first connecting means to said second connecting means and said first connector tubing to said second connector tubing without contaminating grossly the first connector tubing and the second connector tubing.

14. A device according to claim 1 wherein said tube is a catheter.

15. A device, adapted to be secured to a person, for storing liquid material being removed from said person by a tube comprising:
(a) a first container which is secured to said person and is operative to hold said liquid material;
(b) a first valve means secured in the lower longitudinal portion of said first container;
(c) a first connecting means secured to said first valve means;
(d) a first upper closure piece secured in the upper longitudinal portion of said first valve means;
(e) a first front funnel surface, extending from said upper longitudinal portion of said first valve means to the lower longitudinal portion of said first valve means, and secured to said first upper closure piece, which is basically flat when said first valve means is closed and forms a sloping side when said first valve means is open;
(f) a first rear funnel surface, extending from said upper longitudinal portion of said first valve means to said lower longitudinal portion of said first valve means, and secured to said first upper closure piece, which is basically flat when said first valve means is closed and forms a sloping side when said first valve means is open; and
(g) a first metal valve secured at said upper longitudinal portion of said first valve means, and with a chemical coating, with spring tension on said first metal valve holding said first metal valve closed at rest.

16. A device according to claim 15 wherein said first valve means further comprises:
(a) a first securing area within said first valve means; and
(b) a first connector tubing secured within said first securing area and extending out from the bottom of said first valve means.

17. A device, adapted to be secured to a person, for storing liquid material being removed from said person by a tube comprising:
(a) a first container which is secured to said person and is operative to hold said liquid material;
(b) a first valve means secured in the lower longitudinal portion of said first container;
(c) a first connecting means secured to said first valve means;
(d) an inlet port secured to the upper longitudinal portion of said first container and said tube;
(e) a flutter valve secured at the input of said upper longitudinal portion of said first container below said inlet port and operative to prevent contamination from traveling from said first container back toward said inlet port and into said tube; and
(f) a sampling port secured within said inlet port wherein said liquid material entering said inlet port can be removed without contamination of said tube.

18. A device according to claim 17 wherein said first container further comprises a first injection plug secured onto the front section of said first container and operative for solutions to be injected therethrough.

19. A device according to claim 18 wherein said first container further comprises a first disk secured to the rear surface of said first container located opposite from said first injection plug whereby a syringe needle penetrating said first injection plug would hit said first disk and not puncture said rear surface of said first container which would have caused contamination.

20. A device according to claim 19 wherein said first container further comprises a micropore vent secured onto the front section of said first container and operative to allow air into said first container while filtering out bacteria.

21. A device according to claim 17 wherein said first container further comprises a micropore vent secured onto the front section of said first container and operative to allow air into said first container while filtering out bacteria.

22. A device according to claim 17 wherein said first container further comprises a first lower right sloping side, a first lower left sloping side, a first lower right rounded corner and a first lower left rounded corner, all operative to aid in the flow of said liquid material into said first valve means.

23. A device for storing liquid material being removed from a person by a tube comprising:
(a) a first container which is secured to said person and is operative to hold said liquid material;
(b) a first valve means secured in the bottom of said first container;
(c) a first connecting means secured to said first valve means;
(d) a second container operative to be connected to said first container and to store said liquid material when said first valve means is open; and
(e) a second injection plug secured onto the front section of said second container and operative for solutions to be injected therethrough.

24. A device according to claim 23 wherein said second container further comprises a second disk secured to the rear surface of said first container located opposite from said second injection plug whereby a syringe needle penetrating said second injection plug would hit said second disk and not puncture said rear surface of said second container which would have caused contamination.

25. A device for storing liquid material being removed from a person by a tube comprising:
(a) a first container which is secured to said person and is operative to hold said liquid material; p1 (b) a first valve means secured in the bottom of said first container;
(c) a first connecting means secured to said first valve means;
(d) a second container operative to be connected to said first container and to store said liquid material when said first valve means is open; and
(e) a second valve means connected at the bottom of said second container operative for said liquid material to be removed from said second container when said second valve is open comprising:
(1) a second upper closure piece comprising a second metal valve with a chemical coating, with spring tension on said second metal valve holding said second metal valve closed at rest;
(2) a second front funnel surface, secured to said second upper closure piece, which is basically flat when said second valve means is closed and forms a sloping side when said second valve means is open; and (3) a second rear funnel surface, secured to said second upper closure piece, which is basically flat when said second valve means is closed and forms a sloping side when said second valve means is open.

26. A device according to claim 25 wherein said second valve means further comprises:
(a) a second securing area within said second valve means; and
(b) a drainage tubing secured within said second securing area and extending out from the bottom of said second valve means.

27. A device according to claim 26 wherein said device further comprises a first drainage connector secured to the end of said drainage tubing.

28. A device according to claim 27 wherein said device further comprises a second drainage connector secured onto the surface of said second container and operative for said first drainage connector to be secured to when said second valve means is closed and said first drainage connector is not needed, in order to reduce contamination of said first drainage connector and said drainage tubing.

29. A device for storing liquid material being removed from a person by a tube comprising:
(a) a first container which is secured to said person and is operative to hold said liquid material;
(b) a first valve means secured in the bottom of said first container comprising:
(1) a first upper closure piece:
(2) a first front funnel surface, secured to said first upper closure piece, which is basically flat when said first valve means is closed and forms a sloping side when said first valve means is open; and
(3) a first rear funnel surface, secured to said first upper closure piece, which is basically flat when said first valve means is closed and forms a sloping side when said first valve means is open;
(c) a first connecting means secured to said first valve means;
(d) a second container operative to be connected to said first container and to store said liquid material when said first valve means is open;
(e) a first connector tubing secured within said first valve means and extending out from the bottom of said first valve means wherein said first connecting means is secured around said first connector tubing;
(f) a second connector tubing;
(g) a second connecting means secured around second connector tubing;
(h) a first locking mechanism portion secured to said first connecting means;
(i) a second locking mechanism portion secured to said second connecting means whereby said first locking mechanism portion may be secured to said second locking mechanism portion thereby securing said first connecting means to said second connecting means and said first connector tubing to said second connector tubing without contaminating grossly said first connector tubing and said second connector tubing; and
(j) said first container comprising:
(1) an inlet port operative to be secured to said tube;
(2) a flutter valve secured at the input of said first container below said inlet port and operative to prevent contamination from traveling from said first container back toward said inlet port and into said tube; and
(3) a sampling port secured within said inlet port wherein said liquid material entering said inlet port can be removed without contamination of said tube.

* * * * *